United States Patent [19]

Leuba et al.

[11] Patent Number: 4,918,016

[45] Date of Patent: Apr. 17, 1990

[54] ENZYME IMMOBILIZATION ON MINERAL PARTICLES COATED WITH CHITOSAN

[75] Inventors: Jean-Louis Leuba, Boussens; Albert Renken, Saint-Sulpice; Erwin Flaschel, Chavannes, all of Switzerland

[73] Assignee: Nestec S.A., Vevey, Switzerland

[21] Appl. No.: 436,423

[22] Filed: Oct. 25, 1982

[30] Foreign Application Priority Data

Nov. 17, 1981 [CH] Switzerland .................... 7375/81

[51] Int. Cl.$^4$ .................. C12N 11/14; C12N 11/02; C12N 11/10; C12N 11/06
[52] U.S. Cl. ..................... 435/176; 435/177; 435/178; 435/181
[58] Field of Search ............... 435/174, 176, 177, 178, 435/181

[56] References Cited

U.S. PATENT DOCUMENTS

| | | | |
|---|---|---|---|
| 3,909,358 | 9/1975 | Stanley et al. | 435/178 |
| 4,048,018 | 9/1977 | Coughlin et al. | 435/181 X |
| 4,089,746 | 5/1978 | Masri et al. | 435/178 |
| 4,094,743 | 6/1978 | Leuba | 435/178 |
| 4,167,447 | 9/1979 | Masri et al. | 435/178 |
| 4,266,029 | 5/1981 | Branner-Jorgensen | 435/176 |
| 4,336,161 | 6/1982 | Rosevear et al. | 435/178 X |

*Primary Examiner*—David M. Naff
*Attorney, Agent, or Firm*—Vogt & O'Donnell

[57] ABSTRACT

Enzymatic catalysts are produced from mineral particles coated with chitosan. The enzymes may be directly absorbed onto the surface after a cross-linking treatment to stablize the coating or immobilized by chemical bonds after a treatment with a bifunctional reagent, for example with glutaraldehyde. The stability of the biocatalyst is advantageously increased by retreatment with a bifunctional reagent after immobilization of the enzyme. Enzymes sensitive to glutaraldehyde are fixed by a carbodiimide. The catalysts thus prepared are insoluble in aqueous solutions. The particles are rigid and incompressible and are suitable for use in fixed-bed and fluidized-bed reactors. The immobilization yield may reach 90% depending on the circumstances.

12 Claims, No Drawings

ENZYME IMMOBILIZATION ON MINERAL PARTICLES COATED WITH CHITOSAN

BACKGROUND OF THE INVENTION

This invention relates to a process for the production of enzymatically active biocatalysts which re insoluble in aqueous media and which are particularly suitable for use in fluidized-bed or fixed-bed reactors.

The carrying out of enzymatic reactions on an industrial scale has resulted in the appearance of biocatalysts which are insoluble in aqueous media. The reason for this is that the enzymes should not be deactivated after being used only once, which has resulted in their being fixed to an inert support or in their "immobilisation" to enable them to be physically separated from the substance to be treated or "substrate".

Several methods for fixing enzymes to supports have been proposed:

The enzyme is directly adsorbed onto a mineral material, such as ceramics, glass, silica, etc. The products obtained have the disadvantage of being unstable because the enzyme is only weakly fixed to the support.

The enzyme is chemically bound to an organic support, such as a synthetic polymer (for example an aminoethyl cellulose according to British Patent No. 1,357,317) or a natural polymer (for example chitosan according to U.S. Pat. No. 4,094,743) by way of a bifunctional reagent, such as a dialdehyde, or a monofunctional reagent, such as a carbodiimide. The enzymes immobilised on a synthetic support do not have the requisite quality for use in foods. On the other hand, organic supports are not really suited to industrial processes because they are compressible and have a relatively low density and, because of this, they are difficult if not impossible to use in highthroughput fluidised-bed or fixed-bed reactors.

In addition, it is necessary to ensure good contact between the enzyme and the substance to be converted, i.e. the substrate. This means that the enzyme is preferably immobilised on the outer surface and not in the pores or in the matrix of the inert support.

The above-mentioned difficulties and restrictions affecting practical application are more severe if the reaction medium is viscous and contains colloidal or solid substances or impurities. Difficulties such as these are currently being encountered in the food industry.

SUMMARY OF THE INVENTION

We have found an advantageous enzyme immobilisation process which is suitable for use in the food industry and which is not attended by any of the disadvantages referred to above.

The present invention provides a process for the production of an enzymatically active biocatalyst insoluble in aqueous media and particularly suitable for use in fluidised-bed or fixed-bed reactors, which comprises coating particles of a rigid and dense mineral material with a layer of chitosan, stabilising the coated particles with a bifunctional reagent and fixing an enzyme to the support thus treated.

The mineral core used is selected from rigid, chemically inert mineral substances preferably having a porous surface, such as for example microporous particles of silica gel, metal oxides, such as $TiO_2$, $ZrO_2$, ceramics, etc. The particles are generally from 0.05 to 5 mm and preferably from 0.1 to 0.25 mm in diameter.

The core is coated with chitosan which is a natural polymer obtained by the deacetylation of chitin at elevated temperatures in a strongly basic medium. Chitosan is insoluble in water except in the presence of an acid other than sulphuric acid.

Chitin is the principal organic component of the protective exterior of the invertebrates (the carapace of crustaceans or the cuticle of insects) which is also found in the skeletal wall of certain lower forms of vegetable (mushrooms for example). It is a linear polymer of N-acetyle-D-glucosamine which has a high molecular weight (approximately 200,000) and is characterised by bonds of the $\beta(1\rightarrow 4)$ type. Since the N-acetyl group is difficult to eliminate, deacetylation is never complete and generally varies from 50 to 85% in commercial products. It is there products which are known by the name of chitosan.

In order to load the surface of the mineral particles with chitosan, the first step is to prepare an aqueous solution of chitosan in an acid, for example concentrated acetic acid (10 to 80% by weight and preferably 30 to 60% by weight), containing from 1 to 30 g and preferably from 4 to 10 g of chitosan per litre. The mineral particles are then added to the solution while stirring until a concentration of from 10 to 500 g of solid material per litre is obtained. The mixture is the degassed in vacuo, the suspension is left standing for a few hours and, after decantation, the coated particles are recovered by filtration. The particles thus recovered are then washed with water and dried in vacuo. The support thus obtained has substantially the same density as the mineral support, for example 0.33 g/ml in the case of silica gel, i.e. higher than that of chitosan (0.24 g/ml). Compared with chitosan alone, it has decisive advantages from the point of view of industrial application, namely:

It is generally as active in enzymatic units per gram of dry weight as chitosan alone. This is explained by the fact that the active sites of the chitosan are better utilised because they are distributed over the surface of the particles.

By virtue of its higher density, the volume which it occupies in a column is lower than that occupied by chitosan for the same weight or activity.

The mineral core makes the catalyst much harder and more rigid and hence less compressible than chitosan.

The catalyst is suitable for use in a fluidised bed which is compatible with industrial application. During fluidisation, the substrate may be converted by using high throughputs. The treatment of biological fluids (for example milk, whey, etc.) or fluids containing suspended colloids involves far less risk of clogging than fixed-bed treatment. Attempts to fluidise chitosan have been made, but without any success. Aggregates are formed and channelling occurs. The use of chitosan in a fixed bed also involves problems. When the throughput increases, the chitosan, because of its low density, tends to rise and to collect at the column outlet. The internal pressure increases and the process intensifies, resulting in a paid reduction of throughput and in clogging of the column. Another advantage of fluidisation lies in the fact that the particles of catalyst are in a state of permanent agitation in the substrate. Because of this, problems of diffusion are limited and enzymatic activity is maximal.

Handling is much easier than with chitosan.

The particles coated with chitosan are stabilised with a bifunctional reagent preferably selected from linear dialdehydes. The bifunctional reagent may be, for example, malonaldehyde, succinaldehyde, glutaraldehyde, adipaldehyde. It is preferred to use glutaraldehyde which has the advantage of being a readily available commercial product. The object of this operation is to "stabilize" the chitosan and/or to form a network of polymer around the layer of chitosan in order to fix it to the mineral core and to prevent the mineral core from peeling.

DETAILED DESCRIPTION OF THE INVENTION

In a first embodiment of the process which may be used when the enzyme is not sensitive to glutaraldehyde, i.e. does not lose its catalytic properties in the presence of glutaraldehyde, the support is introduced into an aqueous solution of glutaraldehyde having a concentration of up to 25% by weight. Enzymes which are not sensitive to glutaraldehyde include those which do not contain a thiol group in their active site. The treatment is preferably carried out at ambient temperature at a pH value in the range from 2 to 8, preferably in a buffer solution. The duration of the treatment depends upon the concentration of glutaraldehyde and generally amounts to between 31 minutes and a few hours. The whole is left to react, preferably in the absence of air, for example in vacuo, and the excess glutaraldehyde is eliminated by washing with water. The concentration and the reaction time are such that the surface of the support is covered with aldehyde groups chemically bound thereto, the fixed glutaraldehyde making up from 0.5 to 5% of the weight of the support, for example when the support is a silica gel. The support is thus stabilised.

The enzyme containing functional groups capable of reacting with the free aldehyde groups of the stabilised support, for example the free amino groups carried by the lysine bonds, is then fixed by bringing the activated support into contact with an aqueous solution of the enzyme. The pH value of the enzyme solution has to be kept in the stability range of the enzyme used, for example by means of a suitable buffer solution. The reaction normally takes place at ambient temperature, a low temperature only having to be maintained in the case of sensitive enzymes. The non-fixed enzyme is then eliminated by washing with a buffer solution. To obtain a particularly stable catalyst, which is preferred when the catalyst is used in the form of a fluidised bed, the support already loaded with the enzyme may be subjected to an additional treatment with a bifunctional reagent, preferably glutaraldehyde, for example in the form of an aqueous solution having a concentration of up to 25% by weight. The effect of this additional treatment is to crosslink the whole and also to strengthen the bond between the enzyme and the support.

A second embodiment of the process is carried out in cases where the enzyme loses its catalytic properties in the presence of glutaraldehyde, for example in the case of a yeast lactase containing thiol groups sensitive to oxidising agents. The support coated with chitosan and crosslinked as described above is treated by introduction into a solution containing from 0.01 to 1% by weight of glutaraldehyde and by reacting the free aldehyde groups with a compound containing an amine group, such as glycine, asparagine or lysine or, preferably, by reducing the free aldehyde groups, with sodium borohydride for example. After the aldehyde groups have been inactivated, the support is brought into contact with an enzyme, for example a yeast lactase, previously protected at the active site by a competing inhibiting compound, such as for example galactono-γ-lactone or glucono-γ-lactone in a concentration of from 20 to 50 mg/ml of reaction medium. This protective sugar does not affect the adsorption of the enzyme onto the support and is freed by an excess of lactose. The treatment is carried out in a suitable buffer solution, generally at a low temperature, for example in the range from 2 to 10° C., over a period of from 30 minutes to 24 hours, and the excess of enzyme is removed by washing with a buffer solution and then with water.

In order to increase the stability of the enzyme, the enzyme is preferably bound chemically to the chitosan through a coupling agent, such as for example a carbodiimide or Woodward's reagent, 3-(2-ethyl-5-isoxazolo)-benzene sulphonate, which is capable of activating the carboxyl groups of the enzyme and of making them react with the free amino groups of the chitosan. The reaction takes place over a period of 1 to 48 hours at a temperature of from 2 to 25° C. and at a pH value kept in the range from 4 to 6.5 using from 10 to 50 mg of carbodiimide per ml of reaction medium. On completion of the reaction, the excess reagent and the urea produced by the reaction are removed by washing with a suitable buffer solution and then with water. Alternatively, instead of working in stages, the support, the inhibiting compound, the enzyme and the carbodiimide may be contacted at one and the same time.

The product obtained by the process according to the invention has an enzymatic activity approaching that of the corresponding free enzyme - a property which is rarely preserved in conventional fixing processes. In addition, the product remains stable for several months and has a higher inactivation temperature than the corresponding free enzyme.

As mentioned above, the product obtained by the process according to the invention may be used in enzymatic reactions instead of the corresponding free enzyme either in the form of a fixed bed (column) or, preferably, in the form of a fluidised bed. Its use in the food industry should not present any problems because chitosan is a natural organic substance.

EXAMPLES

The process according to the invention is illustrated by the following Examples in which the quantities and percentages quoted are by weight unless otherwise indicated.

EXAMPLE 1

Loading of the support with chitosan 8 g of chitosan are dissolved in 300 ml of concentrated acetic acid and 400 ml of water. The mixture is stirred for 1 hour at 40° C. and then filtered through a cloth filter (106 μm) to eliminate the undissolved residues. The chitosan solution is placed in a desiccator and 120 g of a silica gel, particle diameter $d_p$ 100–125 μm, pore volume 1.2 ml/g, specific surface 320 m²/g) are added to it with gentle stirring which produces some foam. The resulting suspension is then left standing in a vacuum until the foam disappears. After leaving the mixture to stand overnight, the liquid is decanted and the silica gel coated with chitosan is recovered by filtration. After the silica gel has been gently washed with water, the support is oven-dried in vacuo overnight at a temperature of 70° C.

Preparation of a stabilized immobilization support 120 g of the above support (silica gel coated with chitosan) are introduced into a desiccator with 1600 ml of an aqueous solution containing 200 ml of a 25% glutaraldehyde solution. The suspension is gently stirred and then placed under a vacuum. After degassing, the suspension is left standing at atmospheric pressure for 2 hours during which it is periodically subjected to gentle stirring. The support is thus activated, which is reflected in a change in its colour from white to yellow-orange.

The support is recovered by filtration and then carefully washed with water.

Immobilization of invertase on the stabilized support

A solution of 15 mg of invertase (Maxinvert 200,000, a product of Gist-Brocades NV) in 100 ml of water is prepared and the pH value adjusted to 4 with a 0.1 M solution of HCl. 30 ml of this solution are mixed with 3 g of moist activated support prepared as described above. After the suspension has been gently stirred for 2 hours, the catalyst is recovered by filtration. The quantity of active enzyme is determined by measuring the hydrolytic activity on cane sugar. The 30 ml of initial solution contain 4.5 mg of invertase, the filtrate after fixing 0.48 mg and the catalyst 4.02 mg. The immobilisation yield amounts of 89%, no loss of activity during this process being detectable.

EXAMPLE 2

Re-treatment of invertase 15 g of the moist catalyst prepared in accordance with Example 1 and containing 16 mg of active invertase is treated for 2 hours with a 1% solution of glutaraldehyde, the mixture being gently stirred, and the catalyst is recovered by filtration. After washing, the activity of the catalyst measured as described in Example 1 corresponds to 14 mg of active invertase, representing a yield of 87%.

EXAMPLE 3

Immobilization of a fungal lactase on a stabilized support 28 g of moist support activated in accordance with Example 1 are introduced into a glass column having a diameter of 2.5 cm and a height of 20 cm. The column is part of a recycling system equipped with an adjustable peristaltic pump and with a reservoir of which the contents are stirred by a magnetic stirrer. The inlet of the pump is connected to the reservoir whilst its outlet is positioned at the base of the column. The outlet at the head of the column returns the medium to the reservoir. This system is filled with 120 ml of an acidified aqueous solution having a pH value of 4. The pump is adjusted until the support is fluidised to a maximum height of 15 cm in the column. 0.6 g of lactase of *Aspergillus niger* (Rapidase, France, 200,000 units/g) are dissolved in the reservoir with the recirculation system in operation and the support is left in the fluidised state for 2 hours. Activity analysis carried out as described in Example 1 shows that 72% of the activity is present on the support whilst 20% remains in the filtrate after filtration and washing of the catalyst.

EXAMPLE 4

Re-treatment of the immobilized fungal lactase 10 g of the moist lactase catalyst prepared in accordance with Example 3 are mixed with 50 ml of an aqueous solution containing 5% of glutaraldehyde and adjusted to a pH value of 4. This mixture is periodically stirred and the catalyst is recovered by filtration after 2 hours. Analysis of the activity of the catalyst (by hydrolysis of lactose) before the re-treatment indicates an activity corresponding to 21 mg of lactase preparation (Rapidase, France, 200,000 units per gram) per gram of moist catalyst whereas, after the retreatment, an activity corresponding to 19 mg per gram of moist catalyst is measured. This corresponds to a 90% preservation of activity.

EXAMPLE 5

Immobilization of trypsin on a stabilized support 1 g of silica gel coated with chitosan (as in Example 1) is suspended in 20 ml of sodium acetate buffer (0.5 M; pH 6.0). 5 ml of glutaraldehyde (25% aqueous solution) previously diluted in a ration of 1:1 with the same buffer are then added. This activating treatment is continued for 30 minutes with gentle stirring at ambient temperature (25° C.). The material thus activated is washed several times with distilled water to eliminate the residual glutaraldehyde. 50 mg of crystallised bovine trypsin (Merck) are dissolved in 20 ml of sodium borate buffer (0.1 M; pH 8.0) containing calcium chloride (20 mM). The trypsin solution is then added to the chitosan-coated silica gel prepared before hand. The whole is then left standing overnight at 4° C. with gentle stirring (rotary stirrer). The enzyme-coated support is then separated from the solution by centrifuging or filtration and washed several times in succession with a) sodium borate buffer (0.1 M; pH 8.0) containing sodium chloride (0.15 M), b) sodium borate buffer (0.1 M; pH 8.0) and c) distilled water until the adsorption at 280 nm (UV spectrometer) of the wash waters is zero. The enzymatic activity of the soluble trypsin is determined using as substrate N-α-benzoyl-L-arginine-p-nitroanilide (L-BANA) hydrochloride in a concentration of 1 mM in (tris-hydroxymethyl-aminomethane)-HCL buffer (50 mM; pH 8.0) at a temperature of 25° C. The p-nitroaniline released by the enzymatic hydrolysis reaction is determined by UV spectrophotometry at 405 nm. 1 unit of trypsin activity (1IU) corresponds to the quantity of enzyme which releases 1 micromole of p-nitroaniline per minute under the prevailing conditions. The activity of the immobilised trypsin is determined by the same method, but in a stirred bed, using an intermittent measuring apparatus similar to that described in Methods in Enzymology, 44, 344–345 (1976). The quantity of enzyme fixed to the support is indirectly obtained by calculating the difference between the quantity of enzyme initially added and the quantity of enzyme which remains unfixed on the basis of the protein concentrations determined by the Folin-Lowry method (J. Biol. Chem. 193, 265, 1951). The preparation obtained contains 35.2 mg of trypsin per gram of support and has an enzymatic activity of 72 international units (IU) per gram of support. The fixing yield amounts to 63.7%. The specific activity of the immobilised trypsin amounts to 2.04 IU/mg of immobilised enzyme wheras the specific activity of the soluble enzyme amounts to 2.26 IU/mg.

EXAMPLE 6

Stabilization of the support for the immobilization of enzymes sensitive to glutaraldehyde 40 g of support coated with chitosan in accordance with Example 1 are dispersed in 150 ml of potassium phosphate buffer (50 mM; pH 6.5). 1.5 ml of glutaraldehyde (25% aqueous solution, Fluka AG, pract.) are added and the whole left to react for 30 minutes at ambient temperature with gentle rotary stirring. The support is then separated from the solution by filtration (50 μm mesh metal screen) or centrifuging and is then washed repeatedly with distilled water. The support is re-suspended in 150 ml of the above-mentioned buffer. 500 mg of solid sodium borohydride are added in portions. The whole is then left to react for 30 minutes under the same conditions. The support is recovered by filtration, washed with distilled water, centrifuged and then used for the immobilisation of enzymes as described in Examples 7 and 8 below.

EXAMPLE 7

Immobilization of a neutral yeast lactase by adsorption 40 g of support stabilised in accordance with Example 6 are dispersed in 150 ml of potassium phosphate buffer (50 mM; pH 6.5) containing 0.1 mM of manganese chloride and 0.02% of sodium oxide. D-galactono-γlactone (Kock-Light Lab.) is added in a final concentration of 0.1 M. The pH value of the medium is adjusted to 6.5 if necessary. 6 ml of a solution of yeast lactase (Maxilact LX 5000, a product of GistBrocades NV) are then added, after which the medium containing the enzyme and the support is stirred for 16 hours. The support is separated from the medium by filtration and then washed successively with 500 ml of potassium phosphate buffer (50 mM; pH 6.5) and 0.1 mM manganese chloride; 500 ml of the same buffer additionally containing 50 mM of potassium chloride; distilled water (3 x 500 ml). The support having lactase activity is stored in the buffer first mentioned (phosphate-manganese-azide).

The soluble and the immobilised enzymatic activity are determined by UV spectrophotometry using as substrate a 5 mM solution of o-nitrophenyl-β-galactopyranoside (ONPG) at 30° C. The o-nitrophenol released by the enzyme is determined at 405 nm ($\epsilon_M$ $\theta NP$:1097 $M^{-1}cm^{-1}$ at pH 6.5). The activity of the immobilised enzyme is determined as described in Example 5 using the abovementioned substrate. One internal unit (IU) of lactase activity corresponds to the release of one micromole of o-nitrophenol per min. under the conditions indicated. The immobilised lactase has an activity of 423 IU/g of dry support.

EXAMPLE 8

Immobilization of a neutral yeast lactase by covalence

The enzyme adsorbed in accordance with Example 7 may be fixed more firmly to its support by an additional treatment with carbodiimide. After the lactase and its support have been in contact for 30 minutes under the conditions described in Example 7, 2.5 g of carbodiimide 1-cyclohexyl-3-(2-morpholinoethyl)-carbodiimide of metho-p-toluidene sulphonate (Sigma Chemicar Co.) are added in small portions with stirring (rotary stirrer), the pH-value being kept at 6.5 first for 2 hours at ambient temperature and then for 16 hours at 4° C. Washing is then carried out in the same way as in Example 7. The lactase activity of the support determined as in Example 5 amounts to 285 IU/g of dry support.

EXAMPLE 9

Hydrolysis of whey

Deproteinised whey is pumped upwards at 50° C. through the column according to Example 3 filled with catalyst re-treated in accordance with Example 4. An 18% reduction in the activity of the catalyst is observed during the first 12 hours. After this initial reduction, it was found by analysis after one week that the activity of the catalyst remains stable under the treatment conditions specified above.

EXAMPLE 10

Continuous hydrolysis of skimmed milk 90 ml of a biocatalyst suspension according to Example 8 are introduced into a 2.5 cm diameter column. The height of the enzyme bed is 18.3 cm. Sterilised (UHT) skimmed milk is pumped upwards through the column at a rate of 180 ml per hour. Under these conditions, the enzyme bed is fluidised and reaches a height of 25.5 cm. The temperature of the system is kept at 6.2° C., the degree of hydrolysis of the lactose amounting to 92%. After 275 h continuous operation (except for a few hours washing with a suitable detergent every 2 to 3 days), the residual activity of the catalyst is 85% of its initial activity.

We claim:

1. A process for the production of an enzymatically active biocatalyst insoluble in aqueous medium and particularly suitable for use in fluidized-bed or fixed-bed reactors, which comprises coating particles of a rigid and dense mineral material which a layer of chitosan to form a support, treating the support with a bifunctional reagent to stabilise the chitosan and then fixing an enzyme to the support.

2. A process as claimed in claim 1, wherein the bifunctional reagent is glutaraldehyde.

3. A process as claimed in claim 1, wherein the mineral material is selected from a group consisting of porous particles of silica gel, metal oxides and ceramics.

4. A process as claimed in claim 1 or 3, wherein the bifunctional reagent is glutaraldehyde and wherein the enzyme has free amino groups and is not sensitive to glutaraldehyde and is fixed to the stabilised support by chemical binding between free aldehyde groups of the glutaraldehyde and the free amino groups of the enzyme.

5. A process as claimed in claim 4, further comprising treating the enzyme fixed support with glutaraldehyde to increase stability of the enzyme fixed support.

6. A process as claimed in claim 1 or 3, wherein the bifunctional reagent is glutaraldehye and wherein the enzyme is sensitive to glutaraldehyde and further comprising treating the stabilised support with a reducing reagent for enabling the enzyme to be adsorbed onto the stabilised support.

7. A process as claimed in claim 6, wherein the reducing reagent is sodium borohydride.

8. A process as claimed in claim 6, further comprising chemically bonding the adsorbed enzyme to the support with a coupling agent selected from a group consisting of a carbodiimide and Woodward's reagent.

9. A process as claimed in claim 6, further comprising protecting active sites of the enzyme with a sugar which is a protective competing inhibitor which does not affect the adsorption of the enzyme onto the stabilised support and which is freed by an excess of lactose.

10. A process as claimed in claim 9, wherein the protective sugar competing inhibitor is selected from a group consisting of glucono-γ-lactone or galactono-γ-lactone.

11. A process as claimed in claim 1 wherein the chitosan to be coated on the mineral material is in an aqueous solution and which further comprises, after coating the mineral material with the chitosan, drying the support prior to treating the support with a bifunctional reagent.

12. An enzymatically active biocatalyst made by a process as claimed in claim 1.

* * * * *

UNITED STATES PATENT AND TRADEMARK OFFICE
CERTIFICATE OF CORRECTION

PATENT NO. : 4,918,016

DATED : April 17, 1990

INVENTOR(S) : Jean-Louis LEUBA, et al.

It is certified that error appears in the above-identified patent and that said Letters Patent is hereby corrected as shown below:

Column 8, line 35, (line 5 of claim 1) "which" should read --with--.

Signed and Sealed this

Twenty-sixth Day of March, 1991

Attest:

HARRY F. MANBECK, JR.

*Attesting Officer*     Commissioner of Patents and Trademarks